United States Patent …

(12) United States Patent
Nelson et al.

(10) Patent No.: US 11,260,244 B2
(45) Date of Patent: *Mar. 1, 2022

(54) SURGICALLY POSITIONED NEUTRON FLUX ACTIVATED HIGH ENERGY THERAPEUTIC CHARGED PARTICLE GENERATION SYSTEM

(71) Applicant: Westinghouse Electric Company LLC, Cranberry Township, PA (US)

(72) Inventors: John H. Nelson, East McKeesport, PA (US); Michael D. Heibel, Harrison City, PA (US)

(73) Assignee: Westinghouse Electric Company LLC, Cranberry Township, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/795,692

(22) Filed: Feb. 20, 2020

(65) Prior Publication Data

US 2020/0188689 A1    Jun. 18, 2020

Related U.S. Application Data

(63) Continuation of application No. 16/102,063, filed on Aug. 13, 2018, now Pat. No. 10,603,510.

(Continued)

(51) Int. Cl.
*A61N 5/10* (2006.01)
*A61K 41/00* (2020.01)

(52) U.S. Cl.
CPC .............. *A61N 5/10* (2013.01); *A61K 41/009* (2013.01); *A61N 2005/109* (2013.01); *A61N 2005/1094* (2013.01); *A61N 2005/1098* (2013.01)

(58) Field of Classification Search
CPC ................ A61N 5/10; A61N 2005/109; A61N 2005/1094; A61N 2005/1098; A61K 41/009
See application file for complete search history.

(56) References Cited

U.S. PATENT DOCUMENTS 7,022,136 B2   4/2006  Lundqvist
9,528,952 B1  12/2016  Heibel
(Continued)

FOREIGN PATENT DOCUMENTS

EP   1232771 A1   8/2002
EP   2979728 A1   2/2016
(Continued)

OTHER PUBLICATIONS

Written Opinion for International PCT Application No. PCT/US2018/046474, dated Oct. 30, 2018.

(Continued)

*Primary Examiner* — Nicole M Ippolito
*Assistant Examiner* — Hanway Chang
(74) *Attorney, Agent, or Firm* — K&L Gates LLP

(57) ABSTRACT

A process for treating highly localized carcinoma cells that provides precise positioning of a therapeutic source of highly ionizing but weakly penetrating radiation, which can be shaped so that it irradiates essentially only the volume of the tumor. The intensity and duration of the radiation produced by the source can be activated and deactivated by controlling the neutron flux generated by an array of electrically controlled neutron generators positioned outside the body being treated. The energy of the neutrons that interact with the source element can be adjusted to optimize the reaction rate of the ionized radiation production by utilizing neutron moderating material between the neutron generator array and the body. The source device may be left in place (Continued)

and reactivated as needed to ensure the tumor is eradicated without exposing the patient to any additional radiation between treatments. The source device may be removed once treatment is completed.

20 Claims, 1 Drawing Sheet

Related U.S. Application Data

(60) Provisional application No. 62/545,522, filed on Aug. 15, 2017.

(56) References Cited

U.S. PATENT DOCUMENTS

| | | | |
|---|---|---|---|
| 9,636,524 | B2 | 5/2017 | Pantell et al. |
| 10,646,724 | B2 | 5/2020 | Hoedle et al. |
| 2002/0058853 | A1 | 5/2002 | Kaplan |
| 2002/0103410 | A1 | 8/2002 | Munro, III et al. |
| 2012/0330084 | A1 | 12/2012 | Pantell et al. |

FOREIGN PATENT DOCUMENTS

| | | |
|---|---|---|
| WO | 0076557 A1 | 12/2000 |
| WO | 0160141 A2 | 8/2001 |
| WO | 0170336 A1 | 9/2001 |
| WO | 2013003343 A2 | 1/2013 |
| WO | 2013029024 A1 | 2/2013 |
| WO | 2013033249 A2 | 3/2013 |
| WO | 2019036355 A2 | 2/2019 |

OTHER PUBLICATIONS

International Preliminary Report on Patentability for International PCT Application No. PCT/US2018/046474, dated Feb. 18, 2020.
Supplementary European Search Report for corresponding European Patent Application No. EP18845617.2, dated Apr. 7, 2021.

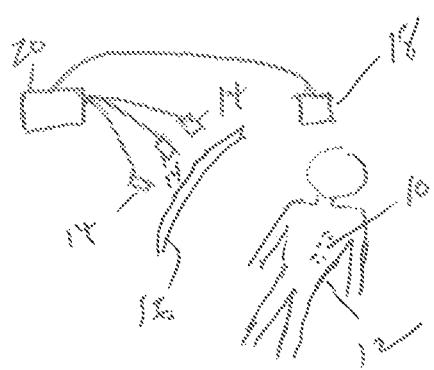

SURGICALLY POSITIONED NEUTRON FLUX ACTIVATED HIGH ENERGY THERAPEUTIC CHARGED PARTICLE GENERATION SYSTEM

CROSS REFERENCE TO RELATED APPLICATION

This application is a traditional application and claims priority to U.S. Provisional Patent Application No. 62/545,522, filed Aug. 15, 2017.

BACKGROUND

1. Field

This invention pertains generally to the treatment of cancer and, more particularly to the treatment of highly localized carcinoma cells.

2. Related Art

The treatment of highly localized carcinoma cells, such as tumors, in the human body using ionizing radiation has proven to be quite effective. However, the application of ionizing radiation to the body typically involves having the radiation used pass through healthy tissue before it arrives at the intended target site. This results in damage to the healthy tissue. This limits the amount of damage that can be done to the tumor at one time, resulting in the need for multiple treatments and the accumulating adverse potential biological consequences and financial costs of the treatments. If the healthy cell damage repair does not keep up with the tumor growth rate and/or metastasis rate to allow for sufficient treatment, the victim is likely to perish from the consequences of the carcinoma.

SUMMARY

This invention overcomes the detrimental effects of the radiation treatment of cancer by providing a method of treating localized carcinoma cells in a body of an animal that includes the step of positioning a therapeutic source that is substantially nonradioactive when not exposed to a neutron source below a given activity, but becomes a source of highly ionizing but weakly penetrating radiation when exposed to a neutron field at or above the given activity, within the body in the vicinity of the carcinoma cells. Preferably, the positioning step surgically implants the therapeutic source material on the carcinoma cells. The therapeutic source is irradiated from outside the body with a neutron field at or above the given activity for a prescribed period of time and the irradiation step is repeated at prescribed intervals. Preferably, the therapeutic source of highly ionizing but weakly penetrating radiation comprises $B_4C$, P-31 or other material that produces comparable high energy alpha or beta particles and either no or low energy gamma radiation. The therapeutic source should be insoluble in water, non-toxic to the body and have short half-lives. Desirably, if $B_4C$ is used, the $B_4C$ is enriched in B-10 content.

In one preferred embodiment the therapeutic source of highly ionizing but weakly penetrating radiation is configured so it substantially only irradiates the carcinoma cells. To achieve that end a radiation shield material is formed on a side of the therapeutic source not facing the carcinoma cells. Preferably, the step of irradiating the therapeutic source includes the step of using an electric neutron generator, such as a Neutristor, to irradiate the therapeutic source. One such embodiment employs a plurality of electric neutron generators positioned around the body to irradiate the therapeutic source from different angles.

In another embodiment the method includes the step of using a neutron moderating material between the electric neutron generator and the therapeutic source to adjust the neutron energy to optimize the highly ionizing, but weakly penetrating radiation produced by the therapeutic source. The neutron moderating material may be $D_2O$, C or other material having similar moderating properties. The neutron moderating material is placed outside the body between the electric neutron generator and the body.

In one such embodiment the therapeutic source is left within the body between treatments of treating the localized carcinoma cells, with the therapeutic source removed from the body once the treatments are complete. The therapeutic source may comprise one or more very thin disks or plates in the order of a micron's thickness with a sufficient combined surface area to ensure the entire volume of localized carcinoma cells will be affected by the highly ionizing but weakly penetrating radiation when one or more of the disks or plates are emplaced around the carcinoma cells and irradiated with the neutron field.

In still another embodiment the method includes the step of using a gamma spectrometer to monitor the intensity of gamma radiation emitted by a product of the neutron radiation of the therapeutic source material while a charged particle production rate can be monitored while the neutron irradiation is occurring. The monitored intensity of the gamma radiation and neutron activity of the neutron field can be used to determine a radiation dose that has been applied to the body. The method may also control the intensity of the neutron field based on the monitored gamma intensity and the radiation dose.

BRIEF DESCRIPTION OF THE DRAWINGS

A further understanding of the invention can be gained from the following description of the preferred embodiments when read in conjunction with the accompanying drawings in which:

FIG. 1 is a schematic of the apparatus that may be employed to practice the method of this invention.

DESCRIPTION OF THE PREFERRED EMBODIMENT

In accordance with this invention for the treatment of highly localized carcinoma cells, one or more very thin (e.g., micron thickness) disks or plates of a therapeutic source with sufficient surface area to ensure that the entire volume of the localized carcinoma cells will be affected by the radiation emitted when one or more devices are implanted within the body of a patient proximate to, and preferably adjacent the tumor. As used herein, the term "patient" means an animal, such as, a human being. The therapeutic source material used should be one that produces high energy alpha or beta particles and either no or low energy gamma radiation. The material must be insoluble in water and non-toxic. The neutron reaction products of the material should also be non-toxic to the subject and have very short half-lives. The use of $B_4C$ for the source material is an example of a material with these qualities and the reference to short half-lives, high energy alpha or beta particles and no or low energy gamma radiation refers to a material that has a half-life approximately as short as or shorter than $B_4C$, alpha or beta particle energy ranges as high or higher than $B_4C$ and no or low gamma radiation energy approximately equal to that of $B_4C$. The preferred embodiment of this material uses $B_4C$ that is enriched in a B-10 content. The use of a compound containing a high concentration of P-31 is another acceptable selection. The therapeutic source material to be inserted for irradiation can be shaped using a number of commercially available fabrication techniques and, preferably, has a shielding over a side of the source material facing away from the carcinoma that is substantially transparent to neutrons, but shields at least some of the highly ionizing particles from the healthy tissue surrounding the carcinoma, such as a light metal-like aluminum.

An array of miniature electrically powered fast neutron generators similar in configuration to the "Neutristor" design developed by Sandia National Laboratory and described in a Snowmass 2013 White Paper entitled *Novel Compact Accelerator Based Neuron and Gamma Sources for Future Detector Calibration*, G. Jennings, C. Sanzeni, D. R. Winn, Fairfield University, Fairfield Conn. 06824, can be used to irradiate the therapeutic source material with a neutron field once the source material is implanted in the patient. Ideally, the array is configured as necessary to provide a neutron intensity at the source position sufficient to maximize the neutron reaction rate without providing too much neutron exposure to other parts of the subject's body. Ideally, the array is geometrically configured to provide neutrons incidents on the carcinoma at different angles to provide the maximum number of sufficiently thermalized neutrons from each generator in the array to reach the target location. This is accomplished through a combination of neutron source array geometry and variations in the thickness of the material used as a neutron moderator placed between the neutron array and the irradiation target. The calculations required to establish the optimum conditions can be performed by those skilled in the art using a number of different commercially available neutron transport calculation products, such as MCNP available from Los Alamos National Laboratory.

FIG. 1 is a schematic that illustrates an apparatus to practice certain methods of this invention. As shown in FIG. 1, a therapeutic source 10 is implanted within the body of a patient 12. An array of electric neutron generators 14 are configured to irradiate with a neutron field the therapeutic source 10 within the patient 12. A neutron moderator 16 is provided that is geometrically configured and placed between each electric neutron generator 14 and the therapeutic source 10 target. The neutron moderator 16 includes a sufficient amount of a material, like $D_2O$ or C, and is independently adjusted to achieve the goal of providing the maximum number of neutrons with the optimum energy for charged particle generation by neutron reactions with the target therapeutic source material.

A gamma spectrometer 18 is provided that measures the intensity of the gamma radiation emitted by the target isotope created in the neutron reaction so the charged particle production rate can be monitored while the neutron irradiation is occurring. This can be accomplished using a number of commercially available devices.

A computational control system 20 uses the measured gamma activity and the activity status of the neutron generators to determine radiation dose that has been applied to the patient relative to a dose target. The control system 20 has the ability to increase or decrease the intensity of the neutrons provided by any or all of the neutron generators in the array based on gamma intensity and measured dose measurements.

The approach and system for treating carcinoma described herein is different from other types of radiation treatments in that it relies on creating and implanting a non-radioactive target in or around a tumor versus the injection of a compound that provides a limited amount of therapeutic treatment deposition in the desired area. The ability this system provides to perform neutron activation of initially non-radioactive materials in a hospital environment maximizes the benefits of charged particle cancer treatment and minimizes the unwanted expense and radiation exposure to the patient and caregivers. This approach allows very precise and efficient cancer killing to occur. Additionally, the target source can be left in position without increasing the whole body radiation dose to the patient, until the tumor is completely dead. Multiple irradiations can occur with relative ease. The use of the electric neutron generator, e.g., Neutristor, provides the ability to perform the treatments in a hospital setting instead of a reactor or very large neutron source location. This greatly reduces treatment costs (or greatly increases treatment profitability) relative to existing radiation treatment methods.

While specific embodiments of the invention have been described in detail, it will be appreciated by those skilled in the art that various modifications and alternatives to those details could be developed in light of the overall teachings of the disclosure. Accordingly, the particular embodiments disclosed are meant to be illustrative only and not limiting as to the scope of the invention which is to be given the full breadth of the appended claims and any and all equivalents thereof

What is claimed is:

1. A method of treating localized carcinoma cells in a body of an animal, the method comprising:
   implanting a device in the body adjacent to the localized carcinoma cells, the device comprising a therapeutic source comprised of a material selected from the group consisting of $B_4C$, P-31, or combinations thereof, wherein the therapeutic source is substantially nonradioactive when not exposed to a neutron source, but becomes a source of highly ionizing but weakly penetrating radiation when exposed to a neutron field at or above a given activity; and
   irradiating the therapeutic source from outside the body with the neutron field at or above the given activity for a prescribed period of time.

2. The method of treating localized carcinoma cells of claim 1 wherein the $B_4C$ is enriched in B-10 content.

3. The method of treating localized carcinoma cells of claim 1 wherein the therapeutic source of highly ionizing but weakly penetrating radiation is configured so it substantially only irradiates the carcinoma cells.

4. The method of treating localized carcinoma cells of claim 3 wherein a radiation shield material that shields at least some of the highly ionizing radiation, but is substantially transparent to neutrons, is formed on a side of the therapeutic source not facing the carcinoma cells.

5. The method of treating localized carcinoma cells of claim 1 wherein implanting the device comprises surgically implanting the therapeutic source approximately on the carcinoma cells.

6. The method of treating localized carcinoma cells of claim 1 wherein irradiating the therapeutic source comprises using an electric neutron generator to irradiate the therapeutic source.

7. The method of treating localized carcinoma cells of claim 6 wherein the electric neutron generator is a Neutristor.

8. The method of treating localized carcinoma cells of claim 6 wherein the electric neutron generator includes a plurality of electric neutron generators positioned around the body to irradiate the therapeutic source from different angles.

9. The method of treating localized carcinoma cells of claim 6 further comprising using a neutron moderating material between the electric neutron generator and the therapeutic source to adjust the neutron energy to optimize the highly ionizing, but weakly penetrating radiation produced by the therapeutic source.

10. The method of treating localized carcinoma cells of claim 9 wherein the neutron moderating material comprises $D_2O$ or C.

11. The method of treating localized carcinoma cells of claim 9 wherein using the neutron moderating material comprises placing the neutron moderating material outside the body.

12. The method of treating localized carcinoma cells of claim 1 further comprising leaving the therapeutic source within the body between treatments of treating the localized carcinoma cells.

13. The method of treating localized carcinoma cells of claim 12 further comprising removing the therapeutic source from the body once treatment of the localized carcinoma cells is completed.

14. The method of treating localized carcinoma cells of claim 1 wherein the therapeutic source comprises one or more very thin disks or plates in the order of a micron's thickness with a sufficient combined surface area to ensure the entire volume of localized carcinoma cells will be affected by the highly ionizing but weakly penetrating radiation when one or more of the disks or plates are emplaced around the carcinoma cells and irradiated with the neutron field.

15. The method of treating localized carcinoma cells of claim 1 wherein the therapeutic source is configured from a material that produces high energy alpha or beta particles and either no or low energy gamma radiation.

16. The method of treating localized carcinoma cells of claim 15 wherein the therapeutic source material is insoluble in water, non-toxic to the body and has short half-lives.

17. The method of treating localized carcinoma cells of claim 1 further comprising using a gamma spectrometer to monitor the intensity of gamma radiation emitted by a product of the neutron radiation of the therapeutic source material while a charged particle production rate can be monitored while the neutron irradiation is occurring.

18. The method of treating localized carcinoma cells of claim 17 further comprising using the monitored intensity of the gamma radiation and neutron activity of the neutron field to determine a radiation dose that has been applied to the body.

19. The method of treating localized carcinoma cells of claim 18 further comprising controlling the intensity of the neutron field based on the monitored gamma intensity and the radiation dose.

20. A method of treating localized carcinoma cells in a body of an animal, the method comprising:
  implanting a device in the body adjacent to the localized carcinoma cells, the device comprising a therapeutic source comprised of a material selected from the group consisting of $B_4C$, P-31, or combinations thereof, wherein the therapeutic source is configurable between:
    a first state, wherein the therapeutic source is substantially nonradioactive; and
    a second state, wherein the therapeutic source is a source of highly ionizing but weakly penetrating radiation in the second state, and wherein the therapeutic source is configured to transition to the second state based on the therapeutic source being exposed to a neutron field at or above a given activity; and
  irradiating the therapeutic source from outside the body with the neutron field at or above the given activity.

* * * * *